United States Patent
Sano et al.

(10) Patent No.: US 10,620,140 B2
(45) Date of Patent: Apr. 14, 2020

(54) X-RAY IMAGING APPARATUS

(71) Applicant: Shimadzu Corporation, Kyoto (JP)

(72) Inventors: Satoshi Sano, Kyoto (JP); Taro Shirai, Kyoto (JP); Takahiro Doki, Kyoto (JP); Akira Horiba, Kyoto (JP); Naoki Morimoto, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 16/121,715

(22) Filed: Sep. 5, 2018

(65) Prior Publication Data
US 2019/0072502 A1    Mar. 7, 2019

(30) Foreign Application Priority Data
Sep. 5, 2017  (JP) .................. 2017-170625

(51) Int. Cl.
| | |
|---|---|
| A61B 6/00 | (2006.01) |
| G01N 23/046 | (2018.01) |
| A61B 6/03 | (2006.01) |
| B29C 70/00 | (2006.01) |
| A61B 6/12 | (2006.01) |
| G01N 23/041 | (2018.01) |

(Continued)

(52) U.S. Cl.
CPC .......... *G01N 23/046* (2013.01); *A61B 6/032* (2013.01); *A61B 6/12* (2013.01); *A61B 6/4291* (2013.01); *A61B 6/484* (2013.01); *A61B 6/5252* (2013.01); *B29C 70/00* (2013.01); *G01N 23/041* (2018.02); *G01N 23/20008* (2013.01); *G01N 23/20075* (2013.01); *G01N 2223/3306* (2013.01)

(58) Field of Classification Search
CPC ........... G01N 23/046; G01N 23/20008; G01N 2223/3306; G01N 23/20075; G01N 23/041; A61B 6/032; A61B 6/4291; A61B 6/484; A61B 6/5252; B29C 70/00
See application file for complete search history.

(56) References Cited

U.S. PATENT DOCUMENTS

2015/0055744 A1* 2/2015 Anton .................... G21K 1/065
                                                          378/36
2015/0323439 A1   11/2015 Monaghan et al.

FOREIGN PATENT DOCUMENTS

WO     2017/032512 A1    3/2017

OTHER PUBLICATIONS

Revol et al., "Laminate fibre structure characterisation of carbon fibre-reinforced polymers by X-ray scatter dark field imaging with a grating interferometer," 2013, NDT&E International, vol. 58, pp. 64-71. (Year: 2013).*

(Continued)

*Primary Examiner* — Kiho Kim
(74) *Attorney, Agent, or Firm* — Muir Patent Law, PLLC

(57) ABSTRACT

The X-ray imaging apparatus is provided with an X-ray source, a plurality of gratings including a first grating and a second grating, a detector, a rotation mechanism for relatively rotating a subject including a fiber bundle and an imaging system, and an image processor for generating a dark field image. The image processor is configured to obtain a three-dimensional dark field image of the subject including at least the fiber bundle from a plurality of dark field images captured at a plurality of rotation angles.

13 Claims, 15 Drawing Sheets

First Embodiment

(51) Int. Cl.
*G01N 23/20* (2018.01)
*G01N 23/20008* (2018.01)

(56) References Cited

OTHER PUBLICATIONS

Tang et al., "X-ray differential phase contrast and dark-field computed tomography and radiography with microbubbles as contrast agent," 2013 IEEE 10th International Symposium on Biomedical Imaging, pp. 1248-1251. (Year: 2013).*

Schaff et al.: "Non-iterative Directional Dark-field Tomography", Scientific Reports, vol. 7, No. 1, Jun. 12, 2017 (Jun. 12, 2017), XP055540825, DOI: 10.1038/s41598-017-03307-6.

Sharma et al.: "Design of Acquisition Schemes and Setup Geometry for Anisotropic X-Ray Dark-Field Tomography (AXDT)", Scientific Reports, vol. 7, No. 1, Jun. 9, 2017 (Jun. 9, 2017), XP055540826, DOI: 10.1038/s41598-017-03329-0.

Revol et al.: "Laminate fibre structure characterisation of carbon fibre-reinforced polymers by X-ray scatter dark field imaging with a grating interferometer", NDT & E International, vol. 58, Sep. 1, 2013 (Sep. 1, 2013), pp. 64-71, XP055540667, GB ISSN: 0963-8695, DOI: 10. 1016/j.ndteint.2013.04.012.

Extended European Search Report dated Jan. 21, 2019 in the corresponding European patent application No. 18191900.2.

* cited by examiner

First Embodiment

First Embodiment

Cross-Sectional View of Subject as Viewed from X-Direction

First Embodiment

Cross-Sectional View of Subject as Viewed from Y-Direction

First Embodiment

First Embodiment

Fiber bundle is arranged in a direction orthogonal to the optical axis of the X-rays First Embodiment Cross-sectional view taken along the line 400-400

First Embodiment

Fiber bundle is arranged obliquely with respect to the optical axis of the X-rays First Embodiment Cross-sectional view taken along the line 500-500

First Embodiment

Tomogram

First Embodiment 3D image (Surface rendering)

First Embodiment

First Embodiment

First Embodiment 3D absorption image

First Embodiment 3D dark field image

Second Embodiment

Second Embodiment

Second Embodiment

Modification of First Embodiment

X-RAY IMAGING APPARATUS

CROSS-REFERENCE TO RELATED APPLICATIONS

The priority application number JP2017-170625, entitled "X-ray imaging apparatus", filed on Sep. 5, 2017, invented by Satoshi Sano, Taro Shirai, Takahiro Doki, Akira Horiba, and Naoki Morimoto, upon which this patent application is based is hereby incorporated by reference.

BACKGROUND OF THE INVENTION

Field of the Invention

The present invention relates to an X-ray imaging apparatus, and more particularly to an X-ray imaging apparatus for imaging a fiber bundle in a subject by performing tomography.

Description of Background Art

Conventionally, an X-ray imaging apparatus for imaging a fiber bundle in a subject by performing tomography is known. Such an X-ray imaging apparatus is disclosed by, for example, "Fiber orientation analysis", [online], [searched on Sep. 5, 2017], Internet <URL: http://www.an.shimadzu.co.jp/ndi/products/x_ryct/smx_225ct_fpd_hr08. htm> (hereinafter referred to as "Non-Patent Document 1").

In recent years, fiber reinforced plastics (FRP) using carbon fibers, glass fibers, etc., have been used in industrial products and sports products. In manufacturing products using FRP, there is a need for a quality inspection device for inspecting the quality, etc., of the manufactured products. Under the circumstances, in the aforementioned Non-Patent Document 1, in order to carry out a detailed inspection of a subject by an absorption image, the subject is imaged under the imaging conditions capable of imaging each of the fibers included in a fiber bundle, and the fibers included in the fiber bundle are directly observed. To do this, it is necessary to reduce the focal spot size of the X-ray source and enhance the resolution of the detector. Specifically, in order to image a single thin fiber in the fiber bundle in the subject, it is necessary to use a micro-focus tube with a small focal spot size as an X-ray source and use a high resolution detector.

However, in the aforementioned Non-Patent Document 1, since the subject is imaged in a magnified manner to observe the fiber bundle, there is a disadvantage that the visual field area of the subject which can be observed at once becomes narrow. For this reason, there is a problem that it is impossible to grasp the entire length of a long fiber bundle and/or the entire shape of the fiber bundle by one imaging. Further, the X-ray imaging apparatus disclosed in Non-Patent Document 1 uses a micro-focus tube having a small focal diameter (high resolution) in order to image fine fibers. Therefore, there is a problem that the dose of X-rays to be irradiated is reduced and therefore the obtained image is less likely to be contrasted.

The present invention has been made to solve the aforementioned problems, and one object of the present invention is to provide an X-ray imaging apparatus capable of imaging a fiber bundle in a subject even when using an X-ray source with a large dose and imaging with a low magnification ratio.

SUMMARY OF THE INVENTION

In order to attain the aforementioned object, an X-ray imaging apparatus according to one aspect of the present invention includes an X-ray source, a plurality of gratings including a first grating for forming a self-image by X-rays irradiated from the X-ray source and a second grating for interfering with the self-image of the first grating, a detector configured to detect the X-rays irradiated from the X-ray source, a rotation mechanism configured to relatively rotate a subject including a fiber bundle and an imaging system constituted by the X-ray source, the detector, and the plurality of gratings, and an image processor configured to generate at least a dark field image from an intensity distribution of the X-rays detected by the detector, wherein the image processor is configured to generate three-dimensional data from a plurality of the dark field images captured at a plurality of rotation angles while relatively rotating the subject and the imaging system by the rotation mechanism and acquire at least three-dimensional dark field image of the subject including the fiber bundle by analyzing X-ray intensity in the generated three-dimensional data. Note that the "dark field image" denotes a visibility image obtained by a visibility change based on small-angle scattering of an object. Further, the dark field image is also called a small-angle scattering image. The "visibility" denotes sharpness.

In the X-ray imaging apparatus according to one aspect of the present invention, as described above, the apparatus further includes the image processor configured to generate three-dimensional data from a plurality of the dark field images captured at a plurality of rotation angles while relatively rotating the subject and the imaging system by the rotation mechanism and acquire at least three-dimensional dark field image of the subject including the fiber bundle by analyzing the X-ray intensity in the generated three-dimensional data. Here, the dark field image is an image that visualizes the microstructure (such as a fiber bundle) in the subject by X-ray diffusion. Therefore, even in cases where fine fibers cannot be resolved in a normal absorption image by imaging conditions, such as, e.g., a focal spot size and a magnification ratio of X-rays, the X-rays are diffused by the fiber bundle, and therefore the fiber bundle can be confirmed according to the dark field image. In other words, it becomes possible to observe the fiber bundle without imaging the subject by magnifying it until a single one fiber contained in the fiber bundle can be imaged. Further, since it becomes possible to image the fiber bundle without magnifying the subject, the subject can be imaged without reducing the dose of the X-ray source. With this, even in the case of using an X-ray source with a large dose and imaging at a low magnification ratio, the fiber bundle in the subject can be imaged.

In the X-ray imaging apparatus according to the aforementioned one aspect of the present invention, the image processor is preferably configured to analyze the X-ray intensity in the generated three-dimensional data to extract the three-dimensional data of the fiber bundle extending in a direction along a grating direction of the plurality of gratings and acquire the three-dimensional dark field image of the subject including the fiber bundle based on the extracted three-dimensional data. Here, the dark field image is an image based on the change of the dose of the X-rays for each pixel of the detector caused by the diffusion of the X-rays. That is, the X-rays transmitted through the gratings and detected by the detector are diffused and the diffused X-rays are absorbed by the grating, and therefore the diffused part of the X-rays becomes undetectable by the detector. On the other hand, since the X-rays which were used to be absorbed by the gratings is diffused, the diffused X-rays pass through the grating, so the X-rays diffused and transmitted through the grating becomes detectable by the detector. Therefore, in the dark field image, the dose of X-rays to be detected in each pixel of the detector changes. When the X-rays are diffused in a direction orthogonal to the grating direction of the grating, the change of the dose of X-rays detected by the detector becomes remarkable. The X-ray diffusion is caused by multiple refraction of X-rays by the microstructure (fiber bundle, etc.) inside the subject. The refraction of X-rays occurs when X-rays pass through the boundary of the area different in refractive index. When the X-rays are refracted by the fiber bundle, the X-rays are refracted by the boundary between the fiber bundle and the other area, so that the X-rays are refracted in a direction intersecting with the direction in which the fiber bundle extends. With this, in the dark field image, it is possible to capture the directivity of the diffusion of X-rays. Therefore, the directivity of the X-ray diffusion by the fiber bundle makes it possible to separate the fiber bundle extending in a specific direction from a fiber bundle or the like extending in another direction. That is, in the dark field image, the fiber bundle extending in a direction along the grating direction of the grating can be extracted in a separable manner from a fiber bundle, etc., extending in a direction other than the grating direction of the grating. Therefore, by extracting the three-dimensional data of the fiber bundle extending in a direction along the grating direction of the grating among the fiber bundles in the subject as described above, the shape and/or the arrangement of the fiber bundle in the subject can be grasped in detail.

In this case, the image processor is preferably configured to extract the three-dimensional data of the fiber bundle from the three-dimensional data generated from the dark field image captured by relatively rotating at least the subject with respect to the imaging system about an axis of a vertical direction orthogonal to a grating direction of the plurality of gratings. Here, by rotating the subject with respect to the imaging system, the incident angle of the X-rays incident on the fiber bundle changes. Compared with the case in which the optical axis of the X-rays and the fiber bundle are perpendicular to each other, in the process of the relative rotation, when the X-rays are incident obliquely to the fiber bundle, an area through which the X-rays transmit the boundary surface between the fiber bundle and the area other than the fiber bundle becomes longer, and the diffusion of the X-rays becomes stronger. Therefore, with the aforementioned configuration, it is possible to image at the angle at which the fiber bundle in the subject most diffuses the X-rays. As a result, in the dark field image, the fiber bundle can be clearly visualized.

In the X-ray imaging apparatus according to the aforementioned one aspect of the present invention, it is preferably configured such that the fiber bundle include the fiber bundles extending in a plurality of different directions in the subject and the image processor is configured to extract the three-dimensional data of the fiber bundles extending in different directions from the three-dimensional data of the dark field image captured by changing either one of the grating direction of the plurality of gratings and an orientation of the subject so that different directions of the subject are along the grating directions of the plurality of gratings. With this configuration, any one of the plurality of fiber bundles in the subject can be arranged along the grating direction of the grating. As a result, in the acquired dark field image, the fiber bundles different in direction can be separately visualized.

In the X-ray imaging apparatus according to the aforementioned one aspect of the present invention, it is preferable to further include a direction changing mechanism configured to change either one of the grating direction of the plurality of gratings and the orientation of the subject. With this structure, by using the direction changing mechanism, for example, an operator can easily change the orientation of the subject and the grating direction of the plurality of gratings without changing the orientation of the subject. As a result, in the dark field image, it is possible to visualize a plurality of fiber bundles extending in different directions included in the subject.

In the X-ray imaging apparatus according to the aforementioned one aspect of the present invention, the image processor is preferably configured to separately extract the three-dimensional data of the plurality of fiber bundles extending in different directions from the three-dimensional data of the dark field image captured plural times while relatively changing the grating direction of the plurality of gratings and the orientation of the subject by the direction changing mechanism and separately generate the three-dimensional dark field image. With this configuration, the dark field image visualizing the plurality of fiber bundles in the subject can be easily generated.

In the X-ray imaging apparatus according to the aforementioned one aspect of the present invention, the image processor is preferably configured to synthesize the plurality of three-dimensional dark field images generated from the plurality of the three-dimensional data based on the fiber bundles extending in mutually different directions. With this configuration, it is possible to confirm a plurality of three-dimensional dark field images based on fiber bundles extending in different directions with one three-dimensional image, so that it is possible to grasp a plurality of fiber bundles in the subject in detail.

In the X-ray imaging apparatus according to the aforementioned one aspect of the present invention, the image processor is preferably configured to analyze the three-dimensional data to determine a boundary between the subject and a background and extract the three-dimensional data of the fiber bundle in a direction along the grating direction of the plurality of gratings. With this configuration, it is possible to easily extract three-dimensional data of the fiber bundle from the obtained three-dimensional data.

In the X-ray imaging apparatus according to the aforementioned one aspect of the present invention, the image processor is preferably configured to obtain a feature amount related to the fiber bundle in the subject, and the feature amount related to the fiber bundle includes at least one or more of a knitting height of the fiber bundle, a size of a gap between adjacent fiber bundles, a width of the fiber bundle, a length of the fiber bundle, a curvature of the fiber bundle, and a thickness of the fiber bundle. With this configuration, it is possible to grasp the shape of the fiber bundle in the subject. As a result, it is possible to confirm whether or not the subject is formed as designed. Here, the knitting height of the fiber bundle denotes a length between a mountain part and a valley part of the knitted part (the intersecting part of fiber bundles) of the fiber bundle. Further, the size of the gap between adjacent fiber bundles denotes a length between one peak (valley) part and the other valley (peak) part of adjacent fiber bundles. A width of the fiber bundle denotes the maximum length of the fiber bundle in the lateral direction. The length of the fiber bundle denotes the maximum length of the fiber bundle in the longitudinal direction. The curvature of the fiber bundle denotes the degree of curvature, etc., at the end surface of the fiber bundle. The thickness of the fiber bundle denotes a length of the fiber bundle in the thickness direction.

In the X-ray imaging apparatus according to the aforementioned one aspect of the present invention, the image processor is preferably configured to highlight boundaries of the fiber bundle and acquire one or more of the number of the fiber bundle in an area-of-interest in the subjects, a distance between boundaries of the fiber bundle, a surface area of the fiber bundles, a density of the fiber bundles based on boundaries of the fiber bundle. With this configuration, it is possible to grasp the quality of the subject by acquiring at least the number of fiber bundles of the subject at the area-of-interest, the distance between the boundaries of the fiber bundle, the surface area of the fiber bundles, and the density of the fiber bundles while making it easy to visually recognize the fiber bundles by highlighting.

In the X-ray imaging apparatus according to the aforementioned one aspect of the present invention, the image processor is preferably configured to perform correction processing including at least smoothing processing on the generated three-dimensional data before acquiring the feature amount. With this configuration, it becomes possible to eliminate noise, etc., contained in the three-dimensional data, so it is possible to extract the fiber bundle with higher accuracy (accurately).

In the X-ray imaging apparatus according to the aforementioned one aspect of the present invention, it is preferably configured such that the plurality of gratings further include a third grating arranged between the X-ray source and the first grating. With this configuration, coherence of the X-rays irradiated from the X-ray source can be enhanced by the third grating. As a result, it is possible to form the self-image of the first grating without depending on the focal length of the X-ray source, so that the freedom of selection of the X-ray source can be improved.

In the X-ray imaging apparatus according to the aforementioned one aspect of the present invention, it is preferably configured to further include a grating moving mechanism configured to move the grating stepwise, wherein the grating moving mechanism is configured to move one of the gratings among the plurality of grating stepwise in a direction orthogonal to the grating direction. With such a configuration, it is possible to easily generate a dark field image by imaging while moving any one of the gratings stepwise in a direction orthogonal to the grating direction in the grating plane.

DESCRIPTION OF PREFERRED EMBODIMENTS

Hereinafter, embodiments of the present invention will be described with reference to the attached drawings.

First Embodiment

With reference to FIG. 1 to FIG. 9, the configuration of an X-ray imaging apparatus 100, the configuration of a subject T, and a method of generating an image including a dark field image by the X-ray imaging apparatus 100 according to a first embodiment will be described.

(Configuration of X-Ray Imaging Apparatus)

Figure 1:
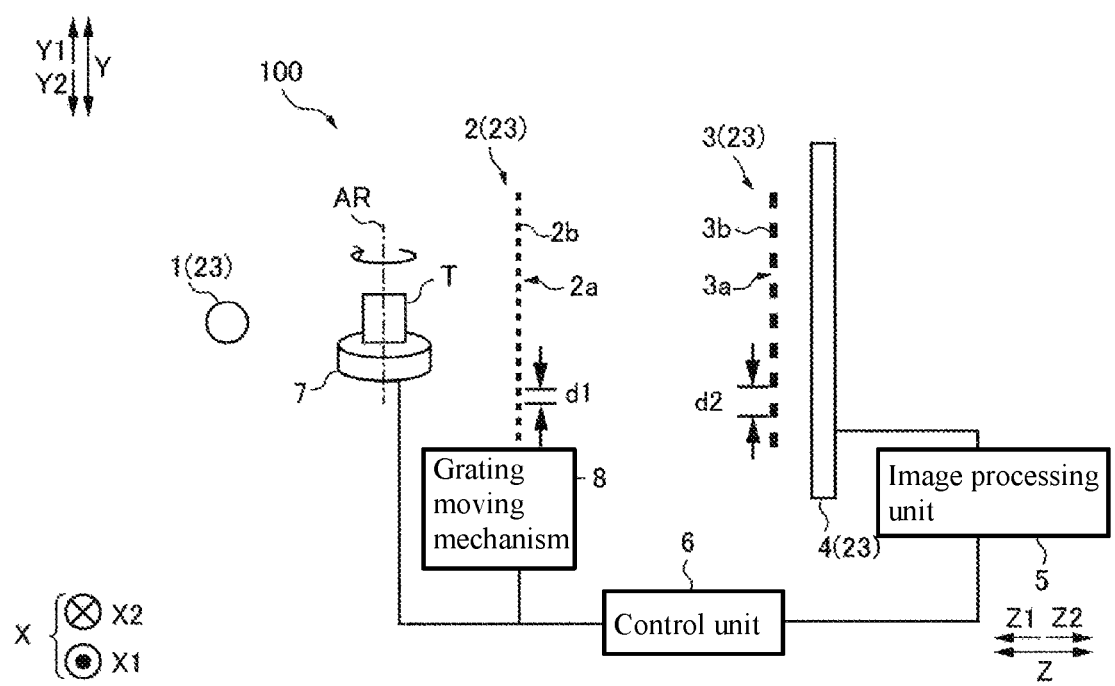
FIG. 1 is a schematic diagram of an X-ray imaging apparatus according to a first embodiment as viewed from a side.

With reference to FIG. 1, first, the configuration of the X-ray imaging apparatus 100 according to the first embodiment of the present invention will be described.

As shown in FIG. 1, the X-ray imaging apparatus 100 is an apparatus for imaging an inside of a subject T by utilizing the diffusion of X-rays passed through the subject T. Further, the X-ray imaging apparatus 100 is an apparatus for imaging the inside of the subject T using a Talbot effect. For example, in a nondestructive inspection application, the X-ray imaging apparatus 100 can be used for imaging the inside of the subject T as an object.

The subject T includes a fiber bundle 10 (see FIG. 2A) therein. The subject T is, for example, a carbon fiber reinforced plastic (CFRP) in which a carbon fiber is used as a fiber bundle 10 and a resin 11 (see FIG. 2A) is used as a base material. Note that the fiber bundle is a bundle of a large number of fibers gathered. In the first embodiment, the fiber bundle 10 is formed in a plate shape by a large number of fibers.

As shown in FIG. 1, the X-ray imaging apparatus 100 is provided with an X-ray source 1, a first grating 2, a second grating 3, a detector 4, an image processing unit 5, a control unit 6, a rotation mechanism 7, and a grating moving mechanism 8. Note that in this specification, the direction from the X-ray source 1 to the first grating 2 is referred to as a Z2-direction, and the direction opposite thereto is referred to as a Z1-direction. The left-right direction in a plane orthogonal to the Z-direction is referred to as an X-direction, the direction toward the rear side of the paper surface is referred to as an X2-direction, and the direction toward the front side of the paper is referred to as an X1-direction. Further note that the up-and-down direction in the plane orthogonal to the Z-direction is referred to as a Y-direction, the upward direction is referred to as a Y1-direction, and the downward direction is referred to as a Y2-direction.

The X-ray source 1 is configured to generate X-rays when a high voltage is applied and irradiate the generated X-rays in the Z2-direction.

The first grating 2 has a plurality of slits 2a and X-ray phase change portions 2b arranged at a predetermined period (pitch) d1 in the Y-direction. The slits 2a and X-ray phase change portion 2b are each formed so as to extend linearly. Further, the slits 2a and the X-ray phase change portion 2b are each formed so as to extend in parallel. The first grating 2 is a so-called phase grating.

The first grating 2 is arranged between the X-ray source 1 and the second grating 3 and configured to be irradiated by the X-rays from the X-ray source 1. The first grating 2 is provided to form a self-image (not shown) of the first grating 2 by a Talbot effect. When X-rays with coherence pass through the grating where the slits are formed, the image of the grating (self-image) is formed at a position away from the grating by a predetermined distance (Talbot distance). This is called a Talbot effect.

The second grating 3 includes a plurality of X-ray transmission portions 3a and X-ray absorption portions 3b arranged in the Y-direction at a predetermined period (pitch) d2. The X-ray transmission portions 3a and the X-ray absorption portions 3b are each formed so as to extend linearly. Further, the X-ray transmission portions 3a and the X-ray absorption portions 3b are each formed so as to extend in parallel with each other. The second grating 3 is a so-called absorption grating. The first grating 2 and the second grating 3 are gratings having different roles, but the slit 2a and the X-ray transmission portion 3a each transmit X-rays. Further, the X-ray absorption portion 3b plays a role of shielding the X-rays, and the X-ray phase change portion 2b changes the phase of the X-rays by the difference of the refractive index with the slit 2a.

The second grating 3 is arranged between the first grating 2 and the detector 4, and is irradiated by the X-rays that passed through the first grating 2. Further, the second grating 3 is arranged at a position away from the first grating 2 by the Talbot distance. The second grating 3 interferes with the self-image of the first grating 2 to form a moire fringe (not shown) on the detection surface of the detector 4.

The detector 4 is configured to detect X-rays, convert the detected X-rays into an electric signal, and read the converted electric signal as an image signal. The detector 4 is, for example, an FPD (Flat Panel Detector). The detector 4 is composed of a plurality of conversion elements (not shown) and a plurality of pixel electrodes (not shown) arranged on the plurality of conversion elements. The plurality of conversion elements and pixel electrodes are arranged in an array manner in the X-direction and Y-direction at a predetermined period (pixel pitch). Further, the detector 4 is configured to output the acquired image signal to the image processing unit 5.

The image processing unit 5 is configured to generate an absorption image 12 (see FIG. 5A) and a dark field image 13 (see FIG. 5A) based on the image signal output from the detector 4. The image processing unit 5 is an image processor and may be comprised of one or more processors, such as, e.g., a GPU (Graphics Processing Unit) and/or an FPGA (Field-Programmable Gate Array) configured for image processing.

The control unit 6 is configured to relatively rotate an imaging system 23 composed of the subject T, the X-ray source 1, the detector 4, and a plurality of gratings including the first grating 2 and the second grating 3 via a rotation mechanism 7. Further, the control unit 6 is configured to move the first grating 2 stepwise in a grating plane in a direction orthogonal to the grating direction via the grating moving mechanism 8. The control unit 6 includes, for example, a processor, such as, e.g., a CPU (Central Processing Unit).

The rotation mechanism 7 is configured to relatively rotate the subject T and the imaging system 23 based on a signal from the control unit 6. Specifically, the rotation mechanism 7 is configured to relatively rotate the subject T with respect to the imaging system 23 by rotating the subject T about the axis AR of the vertical direction orthogonal to the grating direction of the plurality of gratings. The grating direction denotes a direction in which the grating pattern of the grating extends, and in the example shown in FIG. 1, the X-direction is the grating direction. Further, the grating pattern denotes the slit 2a, the X-ray phase change portion 2b, the X-ray transmission portion 3a, and the X-ray absorption portion 3b of each grating. In the example shown in FIG. 1, the direction of the axis AR about which the rotation mechanism 7 rotates the subject T denotes the Y-direction. The rotation mechanism 7 includes, for example, a rotation stage driven by a motor or the like.

The grating moving mechanism 8 is configured to move the first grating 2 stepwise in the direction (Y-direction) orthogonal to the grating direction in the grating plane (in the XY-plane) based on the signal from the control unit 6. Specifically, the grating moving mechanism 8 moves the first grating 2 stepwise by d1/n in which the period d1 of the first grating 2 is divided by "n". The grating moving mechanism 8 is configured to move the first grating 2 stepwise by at least one period d1 of the first grating 2. Here, "n" is a positive integer, for example, 9 or the like. Further, the grating moving mechanism 8 includes, for example, a stepping motor and a piezo actuator.

In the first example, the image processing unit 5 generates an absorption image 12 (see FIG. 5A) and a dark field image 13 (see FIG. 5A) by imaging while moving the first grating 2 stepwise by the grating moving mechanism 8. Here, the absorption image denotes an image of the contrast caused by the difference of the absorption of X-rays by the subject T. Further, the dark field image denotes an image of the contrast caused by the refraction of the X-rays by the microstructure inside the subject T. In the first embodiment, the image processing unit 5 reconstructs the plurality of absorption images 12 and the plurality of dark field images 13 captured while rotating the rotation mechanism 7 to thereby generate a three-dimensional absorption image 20 (see FIG. 9A) and a three-dimensional dark field image 21 (see FIG. 9B).

(Structure of Subject and Direction to Arrange Subject)

Next, with reference to FIG. 2 and FIG. 3, the structure of the subject T and the orientation of the subject T and the grating direction of the grating when imaging the subject T in the X-ray imaging apparatus 100 according to the first embodiment of the present invention will be described.

Figure 2A:
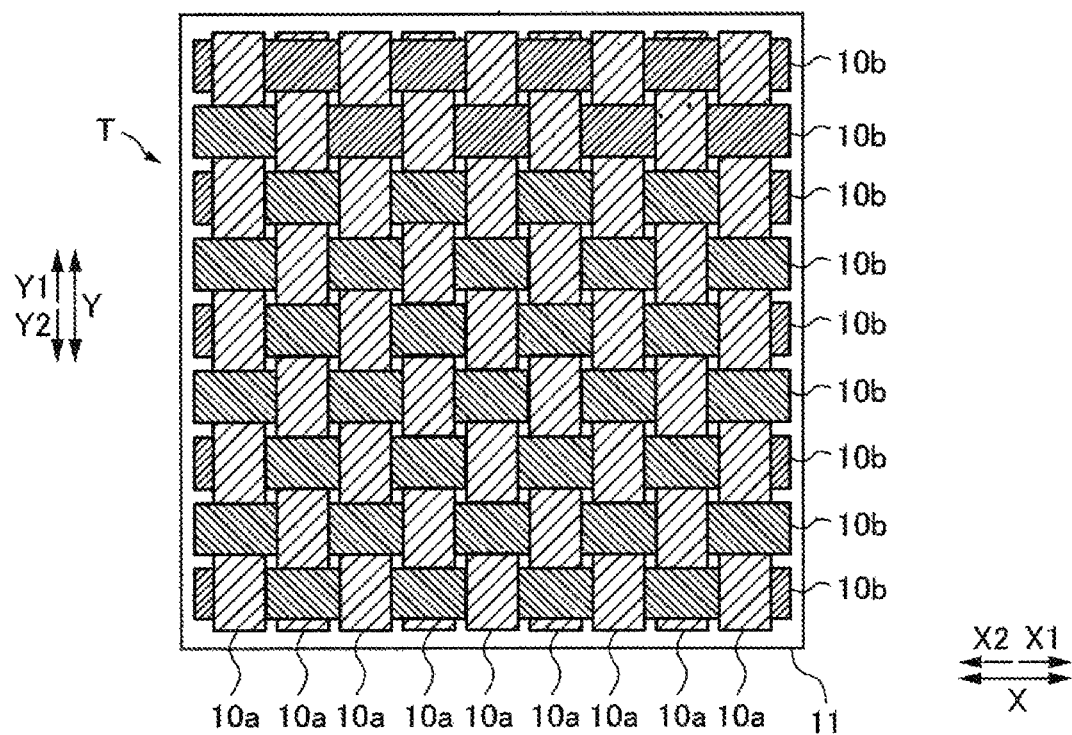
FIG. 2A is a cross-sectional view of the subject as viewed from a Z-direction.

As shown in FIG. 2A, the fiber bundle 10 includes a plurality of fiber bundles 10 extending in different directions in the subject T. In the example shown in FIG. 2A, the subject T has a structure in which the fiber bundle 10a extending in the Y-direction and a fiber bundle 10b extending in the X-direction are knitted. In the example shown in FIG. 2A, the fiber bundle 10a and the fiber bundle 10b are shown in a distinguishable manner, but in reality, they are carbon fibers of the same type woven (or knitted) into a sheet.

Figure 2B:
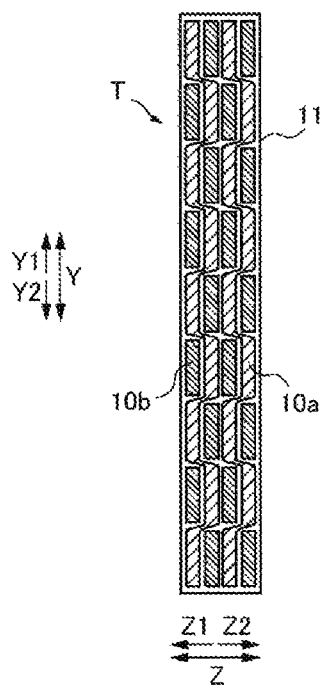
FIG. 2B is a cross-sectional view of the subject as viewed from an X-direction.
Figure 2C:
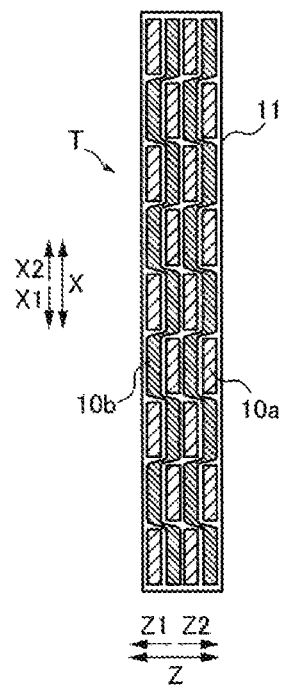
FIG. 2C is a cross-sectional view of the subject as viewed from a Y-direction.

FIG. 2B is a cross-sectional view of the subject T as viewed from the X direction. As shown in FIG. 2B, the fiber bundles 10a extend in the Y-direction and are knitted in the fiber bundles 10b. FIG. 2C is a cross-sectional view of the subject T as viewed from the Y-direction. As shown in FIG. 2C, the fiber bundles 10b extend in the X-direction and are knitted in the fiber bundles 10a. As shown in FIG. 2B and FIG. 2C, the subject T has a structure in which a plurality of sheets in which fiber bundles 10a extending in the Y-direction and fiber bundles 10b extending in the X-direction are knitted is stacked in the Z-direction. Further, the resin 11 which is a base material of the subject T (CFRP) covers the surface of the subject T. Further, the resin 11 fills the gap between the fiber bundles 10 inside the subject T.

Figure 3:
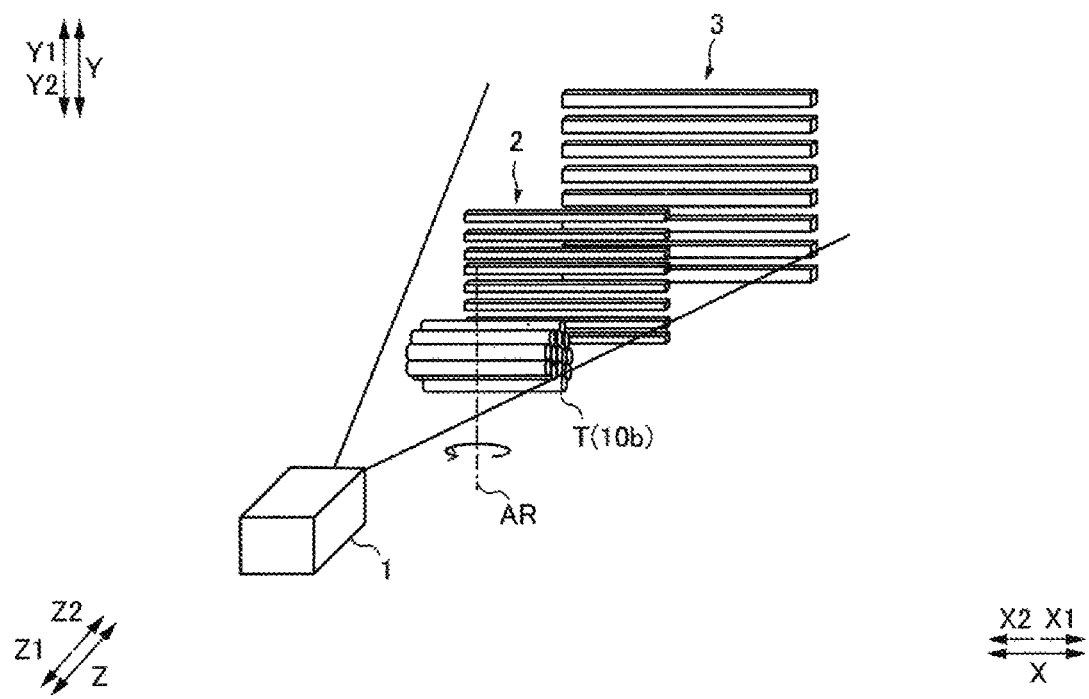
FIG. 3 is a schematic diagram for explaining the arrangement of the gratings and the fiber bundle of the X-ray imaging apparatus according to the first embodiment.

FIG. 3 is a schematic diagram showing the relationship between the subject T and the grating direction of the gratings when the subject T is imaged in the X-ray imaging apparatus 100 according to the first embodiment of the present invention. As shown in FIG. 3, in the first embodiment, the first grating 2 and the second grating 3 are arranged so that the grating directions extend in the lateral direction (X-direction). Further, in FIG. 3, for the sake of convenience, the subject T is illustrated only by the fiber bundles 10b extending in the X-direction. In this arrangement, the fiber bundles 10a are arranged in a direction (Y-direction) orthogonal to the grating direction of the gratings.

(Subject Arrangement Angle and X-Ray Diffusion)

Next, with reference to FIG. 4 and FIG. 5, the arrangement angle of the subject T and the diffusion of X-rays will be described.

Figure 4A:
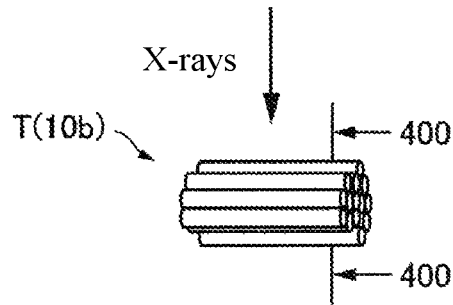
FIG. 4A is a schematic diagram in the case where a subject is arranged in a direction orthogonal to the optical axis of the X-rays in the X-ray imaging apparatus according to the first embodiment.
Figure 4B:
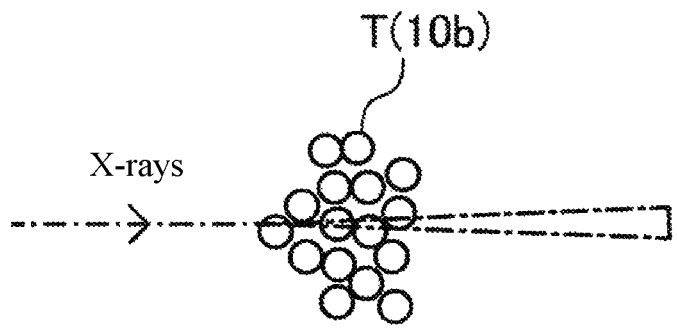
FIG. 4B is a schematic diagram of a cross-sectional view taken along the line 400-400 in FIG. 4A.
Figure 4C:
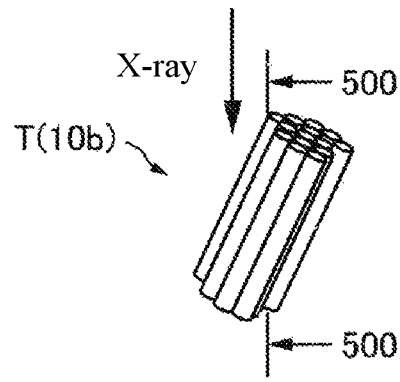
FIG. 4C is a schematic diagram in the case where the subject is arranged in an direction inclined with respect to the optical axis of the X-rays in the X-ray imaging apparatus according to the first embodiment.
Figure 4D:
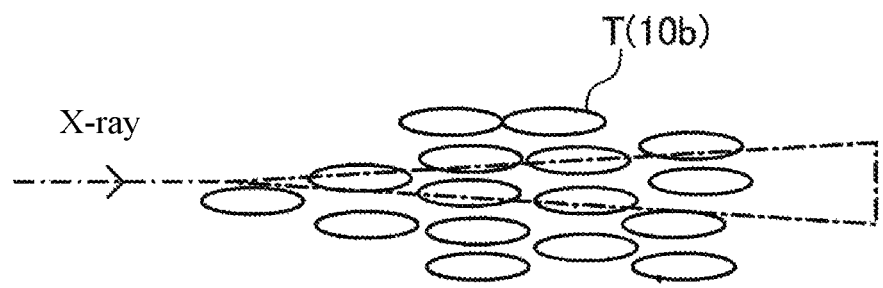
FIG. 4D is a schematic view of a cross-sectional view taken along the line 500-500 in FIG. 4C.

FIG. 4A is a schematic diagram showing an example in which the fiber bundle 10b of the subject T is arranged so as to be orthogonal to the optical axis of the X-rays. FIG. 4B is a cross-sectional view taken along the line 400-400 in FIG. 4A. FIG. 4C is a schematic diagram showing an example in which the fiber bundle 10b of the subject T is arranged so as to be oblique to the optical axis of the X-rays in the XZ-plane. FIG. 4D is a cross-sectional view taken along the line 500-500 in FIG. 4C.

Here, when X-rays are incident on the fiber bundle 10 extending in a direction orthogonal to the optical axis of the X-rays, the X-rays diffuse by the fiber bundle 10. Specifically, at the interface between the fiber in the subject T and the resin 11, the X-rays are refracted by the difference of the refractive index between the fiber and the resin 11. Since the fiber bundles 10 are laminated in the subject T and since the fiber bundle 10 is composed of a large number of fibers, when the X-rays pass through many fibers, multiple refraction occurs and the X-rays diffuse.

In the example shown in FIG. 4A, the fiber bundle 10b is arranged so as to be orthogonal to the optical axis of the X-rays. That is, the fiber bundle 10b is arranged so as to extend in the X-direction. Therefore, as shown in FIG. 4B, the cross-section of the fiber is substantially circular. In the example shown in FIG. 4C, the fiber bundle 10b is arranged obliquely with respect to the optical axis of the X-rays. Therefore, as shown in FIG. 4D, the cross-section of the fiber is elliptical. When the cross-section of the fiber is elliptical, the distance through which the X-rays pass through the interface between the fiber and the resin 11 becomes longer as compared with the case in which the cross-section of the fiber is substantially circular. Further, the interface between the fiber and the resin 11 has a rough shape, and the diffusion of X-rays is increased by the distance that the X-rays pass through the interface between the fiber and the resin 11 becomes long.

FIG. 5 is schematic diagrams A to C showing an absorption image 12 and a dark field image 13 at certain angles (first angle $\theta_1$, second angle $\theta_2$ and third angle $\theta_3$) captured while rotating the subject T in the X-ray imaging apparatus 100 according to the first embodiment. In the absorption image 12a to the absorption image 12c, the fiber bundle 10 absorbs the X-rays regardless of the direction of the fiber bundle 10. For this reason, it is difficult to grasp the detailed structure of the fiber bundle 10 inside the subject T.

In the first embodiment, since the X-rays are diffused by the fiber bundle 10b extending in the X-direction, the structure of the fiber bundle 10b included in the area 14 where the fiber bundles 10 are knitted is visualized in the dark field image 13a to the dark field image 13c. Further, since the fiber bundle 10 and the resin 11 are different in refractive indexes of the X-rays, in the dark field image 13, a contrast is obtained between the fiber bundle 10 and the resin 11. Therefore, in the dark field image 13, the area 15 by the resin 11 is also visualized.

Figure 5A:
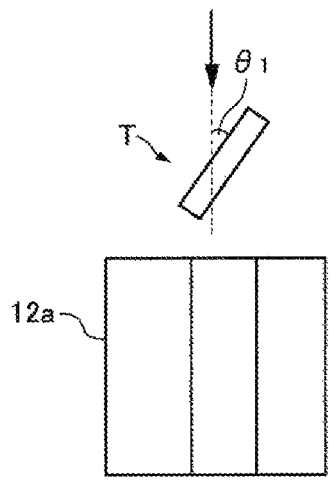
FIG. 5A is a schematic diagram of an absorption image and a dark field image captured by rotating an object at a first angle by the X-ray imaging apparatus according to the first embodiment.
Figure 5B:
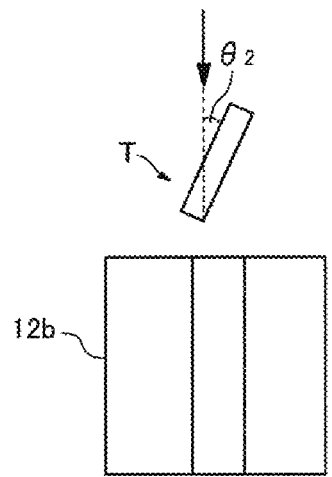
FIG. 5B is a schematic diagram of an absorption image and a dark field image captured by rotating an object at a second angle by the X-ray imaging apparatus according to the first embodiment.
Figure 5C:
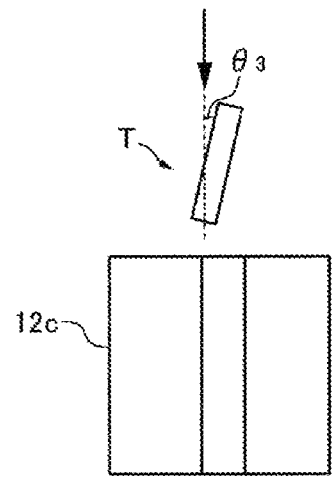
FIG. 5C is a schematic diagram of an absorption image and a dark field image captured by rotating an object at a third angle by the X-ray imaging apparatus according to the first embodiment.

In the example shown in FIG. 5A, since the cross-section of the fiber is elliptical, the diffusion of the X-rays is increased and the structure of the fiber bundle 10b is clearly visualized. However, in the examples shown in FIG. 5B and FIG. 5C, since the angle (second angle $\theta_2$ and third angle $\theta_3$) between the fiber and the optical axis of the X-rays is smaller than in the example shown in FIG. 5A, the cross-section of the fiber approaches a circular shape. Therefore, in the dark field image 13b and the dark field image 13c, the diffusion of the X-rays increases as compared with the dark field image 13a. Therefore, the pixel value of the dark field image 13 becomes too low such that the image is distorted (e.g., crushed) or the resolution of the image is insufficient. As a result, the structure of the fiber bundle 10b may sometimes become unclear.

As described above, when the subject T is rotated, the diffusion of the X-rays increases or decreases according to the relative relationship between the grating direction of the plurality of gratings and the orientation of the subject T. In the first embodiment, since the subject T is rotated one turn, it becomes possible to image at an angle at which the diffusion of the X-rays increases, and it is possible to obtain a dark field image 13 in which the fiber bundle 10 is emphasized.

(Imaging of Subject)

Figure 6:
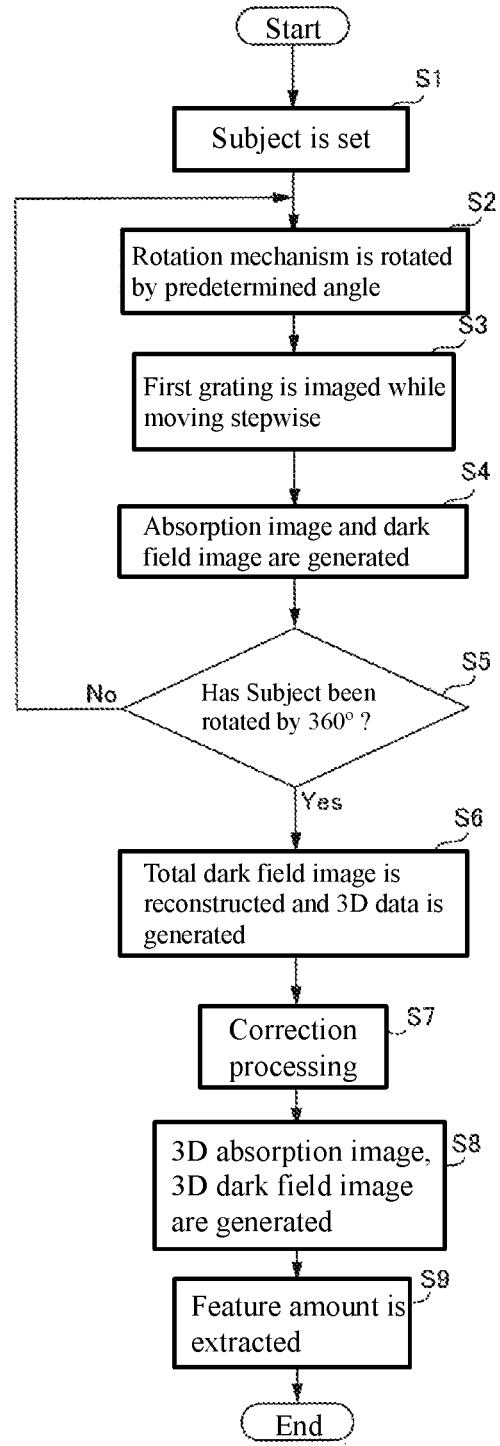
FIG. 6 is a flowchart of an imaging method by the X-ray imaging apparatus according to the first embodiment.

Next, with reference to FIG. 6, the flow of processing for imaging the subject T by the X-ray imaging apparatus 100 according to the first embodiment will be described.

In Step S1, an operator places the subject T on the rotation mechanism 7. Next, in Step S2, the control unit 6 rotates the subject T by a predetermined angle via the rotation mechanism 7.

Next, in Step S3, the control unit 6 images the subject T while moving the first grating 2 stepwise via the grating moving mechanism 8. Next, in Step S4, the image processing unit 5 generates an absorption image 12 and a dark field image 13 of the subject T.

Next, in Step S5, the control unit 6 determines whether or not the rotation mechanism 7 has rotated the subject T by 360 degrees. When the subject T has not been rotated by 360 degrees, it returns to Step S2. When the subject T has been rotated by 360 degrees, it proceeds to Step S6.

In Step S6, the image processing unit 5 reconstructs the absorption image 12 and the dark field image 13 captured in each rotation angle, and generates three-dimensional data (3D data) of the subject T. Next, in Step S7, the image processing unit 5 performs correction processing including at least smoothing processing on the generated three-dimensional data. The smoothing processing includes, for example, smoothing by filtering with a Gaussian filter or the like.

Figure 9A:
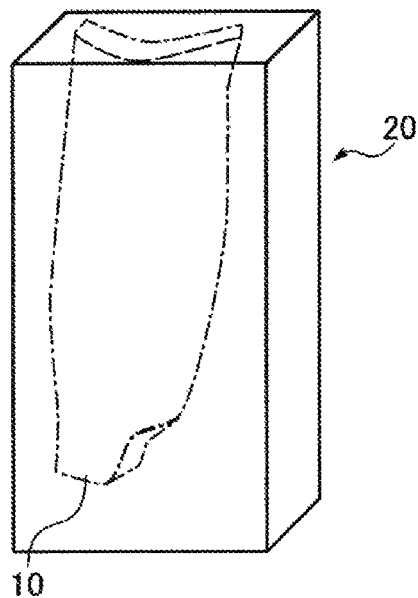
FIG. 9A is a 3D (three-dimensional) absorption image captured by the X-ray imaging apparatus according to the first embodiment.
Figure 9B:
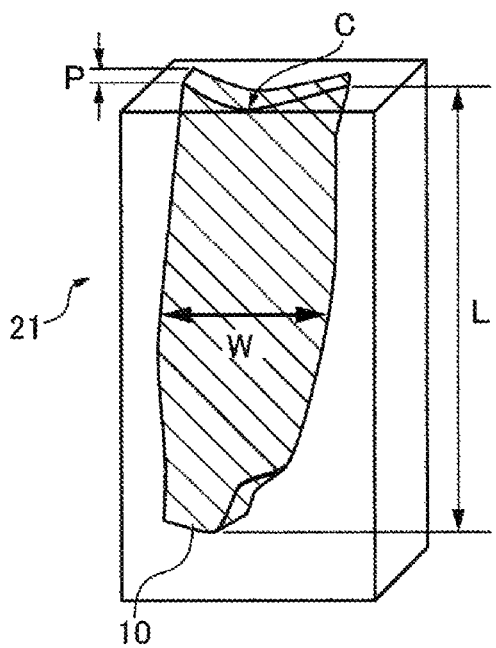
FIG. 9B is a 3D (three-dimensional) dark field image captured by the X-ray imaging apparatus according to the first embodiment.

Next, in Step S8, the image processing unit 5 generates a three-dimensional absorption image 20 (see FIG. 9A) and a three-dimensional dark field image 21 (see FIG. 9B). Specifically, the image processing unit 5 determines the boundary between the subject T and the background by analyzing the generated three-dimensional data. The image processing unit 5 extracts the three-dimensional data of the fiber bundle 10b extending in a direction along the plurality of grating directions. As a result, the image processing unit 5 generates the three-dimensional absorption image 20 and the three-dimensional dark field image 21. A method of determining the boundary between the subject T and the background uses, for example, threshold processing for extracting data whose voxel value of three-dimensional data of the subject T is equal to or more than a predetermined value as data of the fiber bundle 10.

Next, in Step S9, the image processing unit 5 acquires the feature amount of the fiber bundle 10. The feature amount related to the fiber bundle 10 includes at least one or more of the knitting height H of the fiber bundle 10 (see FIG. 8B), the size S of the gap between adjacent fiber bundles 10 (see FIG. 8B), the width W (see FIG. 9B) of the fiber bundle 10, the length L (see FIG. 9B) of the fiber bundle 10, the curvature C of the fiber bundle 10 (see FIG. 9B), and the thickness P of the fiber bundle 10 (see FIG. 9B). To extract the feature amount, for example, a tensor analysis, etc., is used.

(Image Generated by Image Processing Unit)

Next, with reference to FIG. 7 to FIG. 9, an image generated by the image processing unit 5 according to the first embodiment will be described.

In the first embodiment, the image processing unit 5 is configured to extract the three-dimensional data of the fiber bundle 10 extending in a direction along the grating direction of the plurality of gratings. Specifically, the image processing unit 5 is configured to extract the three-dimensional data of the fiber bundle 10 from the three-dimensional data generated from the dark field image 13 captured by relatively rotating the subject T with respect to the imaging system 23 about an axis AR of the vertical direction orthogonal to the grating direction of the plurality of gratings. Further, the image processing unit 5 is configured to determine the boundary between the subject T and the background by analyzing the three-dimensional data and extract the three-dimensional data of the fiber bundle 10 in a direction along the grating direction of the plurality of gratings.

Figure 7A:
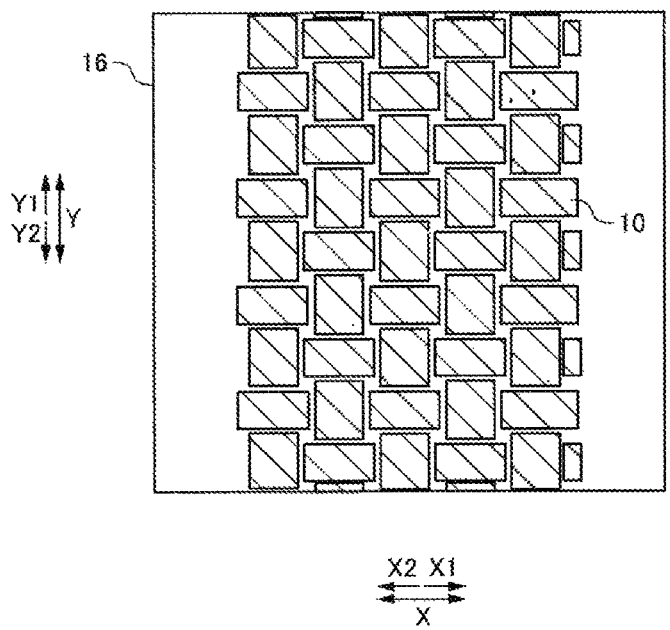
FIG. 7A is a schematic diagram of a tomogram of an absorption image captured by the X-ray imaging apparatus according to the first embodiment.
Figure 7B:
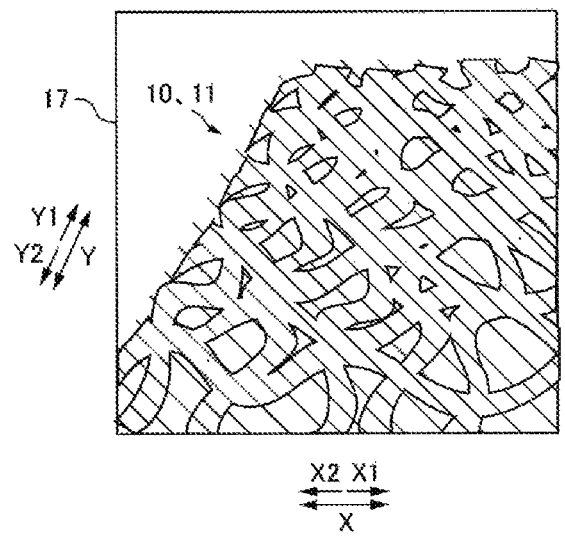
FIG. 7B is a schematic diagram of a 3D (three-dimensional) image captured by the X-ray imaging apparatus according to the first embodiment.

FIG. 7A is a schematic diagram of the tomogram 16 of the three-dimensional absorption image 20. FIG. 7B is a perspective view of the three-dimensional image 17 obtained by imaging the surface of the three-dimensional absorption image 20. As shown in FIG. 7A, in the tomogram 16 of the three-dimensional absorption image 20, X-rays are absorbed irrespective of the extending direction of the fiber bundle 10. Therefore, not only the fiber bundle 10b extending in the X-direction but also the fiber bundle 10a extending in the Y-direction are visualized. Further, as shown in FIG. 7B, the contrast of the fiber bundle 10 and that of the resin 11 become substantially the same in the three-dimensional image 17, which also visualizes the resin 11. Therefore, the knitting shape of the fiber bundles 10 cannot be grasped.

Figure 8A:
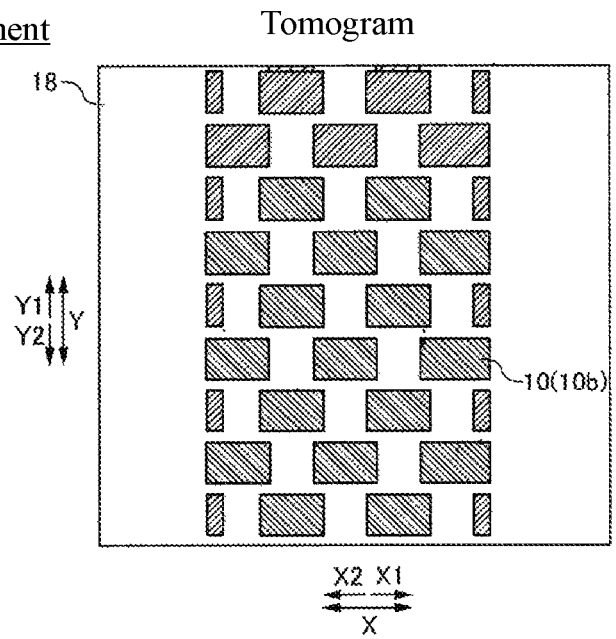
FIG. 8A is a schematic diagram of a tomogram of a dark field image captured by the X-ray imaging apparatus according to the first embodiment.
Figure 8B:
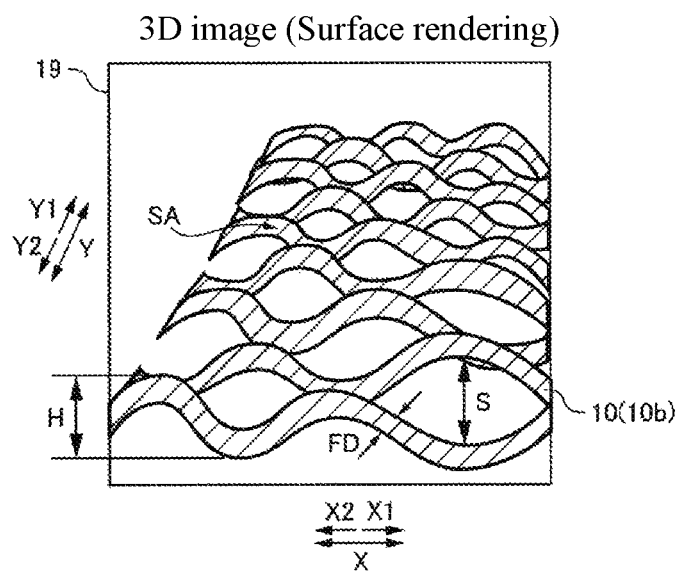
FIG. 8B is a schematic diagram of the 3D (three-dimensional) image captured by the X-ray imaging apparatus according to the first embodiment.

FIG. 8A is a schematic diagram of the tomogram 18 of the three-dimensional dark field image 21. FIG. 8B is a perspective view of the three-dimensional image 19 obtained by imaging the surface of the three-dimensional dark field image 21. As shown in FIG. 8A, in the first embodiment, since the fiber bundles 10b extend in a direction along the grating direction of the plurality of gratings, the diffusion of the X-rays by the fiber bundles 10b increases, which enhances the contrast of the fiber bundles 10b. Therefore, in the tomogram 18 of the three-dimensional dark field image 21, only the fiber bundles 10b extending in the X-direction can be visualized. Further, in the three-dimensional image 19, the knitting structure of the fiber bundles 10b extending in the X-direction can be confirmed. Further, as shown in FIG. 8B, the image processing unit 5 can acquire the knitting height H of the fiber bundle 10 and the size S of the gap between the adjacent fiber bundles 10 as the feature amount of the fiber bundle 10b. The knitting height H of the fiber bundle 10 denotes a length between the peak part and the valley part of the knitted part (the intersecting part of the fiber bundle 10a and fiber bundle 10b) of the fiber bundle 10. The size S of the gap between adjacent fiber bundles 10 denotes a length between one peak (valley) portion and the other valley (peak) portion of the adjacent fiber bundles 10.

Further, as shown in FIG. 8B, the image processing unit 5 is configured to detect the boundaries of the fiber bundle 10 and highlight the boundaries of the fiber bundles 10 in the dark field image 13. In the example shown in FIG. 8B, the image processing unit 5 highlights the boundaries of the fiber bundles 10 by displaying the boundaries of the fiber bundles 10 with a bold line, but the method of highlighting the boundaries of the fiber bundles 10 may be any method. The boundaries of the fiber bundles 10 may be highlighted in the tomogram 18 of FIG. 8A. For example, the boundaries of the fiber bundle 10 may be emphasized by changing the color of the boundaries of the fiber bundle 10. Further, the image processing unit 5 is configured to acquire the number of fiber bundles 10 within the area-of-interest in the subject T, the distance FD between the boundaries of the fiber bundle 10, the surface area SA (the area of the hatched area), and the density of the fiber bundle 10. In this specification, the area-of-interest is an area in which an operator can specify an arbitrary position and a size in three-dimensional data. The number of fiber bundles 10 denotes the number of fiber bundles 10 extending in a direction along the grating direction of the plurality of gratings in the dark field image 13. Further, the distance FD between the boundaries of the fiber bundle 10 is the distance between the boundaries of the opposing fiber bundles 10. Further, in the example shown in FIG. 8A, the density of the fiber bundle 10 denotes the ratio of the area occupied by the fiber bundle 10 (10*b*) in the tomogram 18.

FIG. 9A is a schematic diagram of a three-dimensional absorption image 20 of the subject T in which fiber bundles 10 are not knitted inside the subject T. FIG. 9B is a schematic diagram of a three-dimensional dark field image 21 of the subject T in which fiber bundles 10 are not knitted inside in the subject T. As shown in FIG. 9A, in the three-dimensional absorption image 20, since the contrast between the fiber bundle 10 and the resin 11 is not made substantially, fiber bundles 10 inside the subject T cannot be clearly confirmed. In FIG. 9B, fiber bundles 10 inside the subject T can be confirmed due to the difference of the refractive index between the fiber bundle 10 and the resin 11.

Further, as shown in FIG. 9B, the image processing unit 5 can acquire, as the feature amounts of the fiber bundle 10, the width W of the fiber bundle 10, the length L of the fiber bundle 10, the curvature C of the fiber bundle 10, and the thickness P of the fiber bundle 10. The width W of the fiber bundle 10 denotes the maximum length of the fiber bundle 10 in the transverse direction. The length L of the fiber bundle 10 denotes the maximum length of the fiber bundle 10 in the longitudinal direction. Further, the curvature C of the fiber bundle 10 denotes the degree of curvature at the end surface, etc., of the fiber bundle 10. The thickness P of the fiber bundle 10 denotes the length of the fiber bundle 10 in the thickness direction (Z-direction).

Effects of First Embodiment

In the first embodiment, the following effects can be obtained.

In the first embodiment, as described above, the X-ray imaging apparatus 100 is provided with the X-ray source 1, a plurality of gratings including the first grating 2 for forming a self-image by the X-rays emitted from the X-ray source 1 and the second grating 3 for interfering with the self-image of the first grating 2, the detector 4 for detecting the X-rays irradiated from the X-ray source 1, the subject T including the fiber bundle 10, a rotation mechanism 7 for relatively rotating the subject T including the fiber bundle 10 and the imaging system 23 composed of the X-ray source 1, the detector 4, and the image processing unit 5 for generating at least the dark field image 13 from the intensity distribution of the X-rays detected by the detector 4. The image processing unit 5 is configured to generate three-dimensional data from a plurality of dark field images 13 captured at a plurality of rotation angles while relatively rotating the subject T by the rotation mechanism 7, and acquire at least three-dimensional dark field image 21 of the subject T including the fiber bundle 10 by analyzing the X-ray intensity in the generated three-dimensional data. Here, the dark field image 13 is an image that visualizes the microstructure (such as a fiber bundle 10) in the subject T by X-ray diffusion. Therefore, even in cases where fine fibers cannot be resolved by a normal absorption image 12 by imaging conditions, such as, e.g., the focal spot size of X-rays and the magnification ratio, the X-rays are diffused by the fiber bundle 10, and therefore the fiber bundle 10 can be confirmed according to the dark field image 13. In other words, it becomes possible to observe the fiber bundle 10 without imaging the subject T by magnifying it until a single one fiber contained in the fiber bundle 10 can be imaged. Further, since it becomes possible to image the fiber bundle 10 without magnifying the subject T, the subject T can be imaged without reducing the dose of the X-ray source 1. With this, even in the case of using an X-ray source 1 with a large dose and imaging at a low magnification ratio, the fiber bundle 10 in the subject T can be imaged.

Further, in the first embodiment, as described above, the image processing unit 5 is configured to extract the three-dimensional data of the fiber bundle 10 extending in a direction along the grating direction of the plurality of gratings. Here, the dark field image 13 denotes an image based on the change of the dose of the X-rays for each pixel of the detector 4 caused by the diffusion of the X-rays. That is, the X-rays transmitted through the grating and detected by the detector 4 are diffused and the diffused X-rays are absorbed by the grating, and therefore the diffused part of the X-rays becomes undetectable by the detector 4. On the other hand, as the X-rays which were used to be absorbed by the grating are diffused, the diffused X-rays pass through the grating, so the X-rays diffused and transmitted through the grating becomes detectable by the detector 4. Therefore, in the dark field image 13, the dose of X-rays to be detected in each pixel of the detector 4 changes. When the X-rays are diffused in a direction orthogonal to the grating direction of the grating, the change of the dose of X-rays detected by the detector 4 becomes remarkable. The diffusion of the X-rays is caused by multiple refraction of the X-rays by the microstructure inside the subject T (fiber bundle 10, etc.). The refraction of the X-rays occurs when the X-rays pass through the boundary of the area different in refractive index. When the X-rays are refracted by the fiber bundle 10, the X-rays are refracted by the boundary between the fiber bundle 10 and the resin 11, so that the X-rays are refracted in a direction intersecting with the direction in which the fiber bundle 10 extends. With this, in the dark field image 13, it is possible to grasp the directivity of the diffusion of the X-rays. Therefore, the directivity of the X-ray diffusion by the fiber bundle 10 makes it possible to separate the fiber bundle 10 extending in a specific direction from the fiber bundle 10 or the like extending in another direction. That is, in the dark field image 13, the fiber bundle 10 extending in a direction along the grating direction of the gratings can be extracted in a separable manner from the fiber bundle 10 extending in a direction other than the grating direction of the grating. Therefore, as described above, by extracting the three-dimensional data of the fiber bundle 10 extending in a direction along the grating direction of the grating among the fiber bundle 10 in the subject T, the shape, the arrangement, etc., of the fiber bundle 10 in the subject T can be grasped in detail.

Further, in the first embodiment, as described about, the image processing unit 5 is configured to extract the three-dimensional data of the fiber bundle 10 from the three-dimensional data generated from the dark field image 13 captured by relatively rotating at least the subject T with respect to the imaging system 23 about an axis AR of the vertical direction orthogonal to the grating direction of the plurality of gratings. Here, by rotating the subject T with respect to the imaging system 23, the incident angle of the X-rays incident on the fiber bundle 10 changes. Compared with the case in which the optical axis of the X-rays and the fiber bundle 10 are perpendicular to each other, in the process of the relative rotation, when the X-rays are incident obliquely to the fiber bundle 10, an area through which the X-rays transmit the boundary plane between the fibers and the resin 11 becomes longer, and the diffusion of the X-rays becomes stronger. With this, it is possible to image at the angle at which the fiber bundle 10 in the subject T most diffuses the X-rays. As a result, in the dark field image 13, the fiber bundle 10 can be clearly visualized.

Further, in the first embodiment, as described above, the image processing unit 5 is configured to analyze the three-dimensional data to determine the boundary between the subject T and the background and extract the three-dimensional data of the fiber bundle 10 in a direction along the grating directions of the plurality of gratings. With this configuration, it is possible to easily extract the three-dimensional data of the fiber bundle 10 from the obtained three-dimensional data.

Further, in the first embodiment, as described above, the image processing unit 5 is configured to obtain the feature amount related to the fiber bundle 10 in the subject T, and the feature amount related to the fiber bundle 10 includes at least one or more of the knitting height H of the fiber bundle 10, the size S of the gap between adjacent fiber bundles 10, the width W of the fiber bundle 10, the length L of the fiber bundle 10, the curvature C of the fiber bundle 10, and the thickness P of the fiber bundle 10. With this configuration, it is possible to grasp the shape of the fiber bundle 10 in the subject T. As a result, it is possible to confirm whether or not the subject T is formed as designed.

Further, in the first embodiment, as described above, the image processing unit 5 is configured to highlight the boundaries of the fiber bundles 10 and acquire one or more of the boundary density of the fiber bundle 10 in the area-of-interest in the subject T, the surface area SA of the fiber bundles 10, and the density of the fiber bundle 10 based on the boundaries of the fiber bundles 10. With this configuration, it is possible to grasp the quality of the subject T by acquiring at least the number of fiber bundles of the area-of-interest of the subject, the distance FD between the boundaries of fiber bundles 10, the surface area SA of the fiber bundles 10, the density of the fiber bundles 10 while making it easy to visually recognize the fiber bundle 10 by highlighting.

Further, in the first embodiment, as described above, the image processing unit 5 is configured to perform correction processing including at least smoothing processing on the generated three-dimensional data before acquiring the feature amount. With this configuration, it becomes possible to eliminate noise, etc., contained in the three-dimensional data, so it is possible to extract the fiber bundle 10 with higher accuracy (accurately).

Further, in the first embodiment, as described above, the X-ray imaging apparatus 100 is further provided with a grating moving mechanism 8 for moving the grating stepwise, and the grating moving mechanism 8 is configured to move the first grating 2 stepwise in the grating plane in a direction orthogonal to the grating direction. With such a configuration, it is possible to easily generate the dark field image 13 by imaging while moving the first grating 2 stepwise in a direction orthogonal to the grating direction in the grating plane.

Second Embodiment

Next, the configuration of the X-ray imaging apparatus 200 according to the second embodiment of the present invention will be described with reference to FIG. 10 to FIG. 12. Unlike the first embodiment in which the fiber bundle 10 extending in one direction among fiber bundles 10 in the subject T is extracted, in the second embodiment, the X-ray imaging apparatus 200 is configured to extract a plurality of fiber bundles 10 extending in different directions. The same reference numerals are allotted to the same configurations as those of the first embodiment, and the description thereof will be omitted.

(Configuration of X-Ray Imaging Apparatus)

First, with reference to FIG. 10, the configuration of the X-ray imaging apparatus 200 according to a second embodiment will be described.

Figure 10:
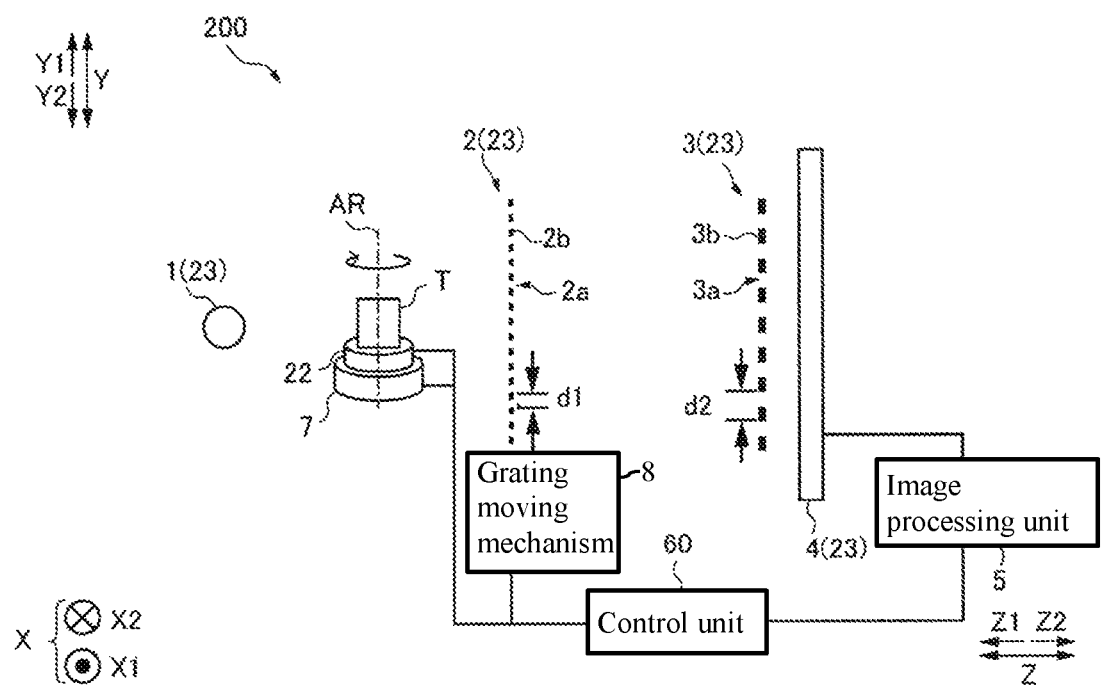
FIG. 10 is a schematic diagram of an X-ray imaging apparatus according to a second embodiment as seen from a side.
Figure 11A:
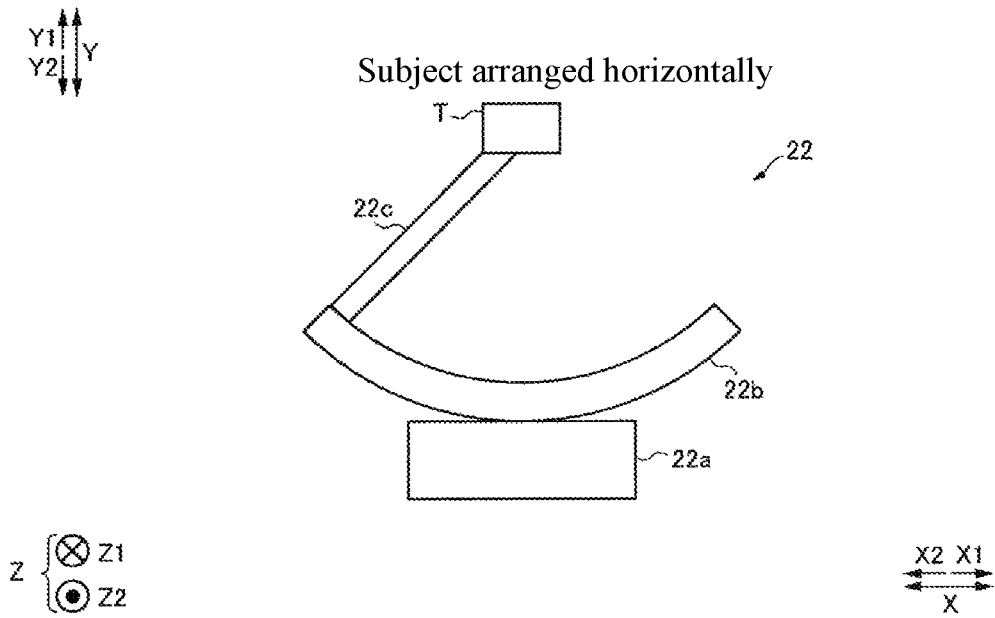
FIG. 11A is a schematic diagram in the case where the subject is arranged horizontally by the direction conversion mechanism according to the second embodiment.

As shown in FIG. 10, the X-ray imaging apparatus 200 in the second embodiment is further provided with a direction changing mechanism 22 for relatively changing the grating direction of the plurality of gratings and the orientation of the subject T. The direction changing mechanism 22 is configured to relatively change the grating direction of the plurality of gratings and the orientation of the subject T based on the signal from the control unit 60. Further, as shown in FIG. 10, in the second embodiment, the direction changing mechanism 22 is arranged on the rotation mechanism 7, and the rotation mechanism 7 relatively rotates the subject T together with the direction changing mechanism 22 about the axis AR.

(Configuration of Direction Changing Mechanism)

Next, with reference to FIG. 11, the configuration of the direction changing mechanism 22 provided in the X-ray imaging apparatus 200 according to the second embodiment of the present invention will be described. As shown in FIG. 11A, the direction changing mechanism 22 includes a drive unit 22a, a frame 22b, and a subject holder 22c.

The drive unit 22a is configured to rotate the subject holder 22c by a predetermined angle based on the signal from the control unit 60. The drive unit 22a includes, for example, a stepping motor and the like. The subject holder 22c is configured to rotate in the XY-plane by the drive unit 22a in the direction along the circumferential direction of the frame 22b. The subject holder 22c is configured such that one end is supported by the frame 22b and the other end holds the subject T.

Figure 11B:
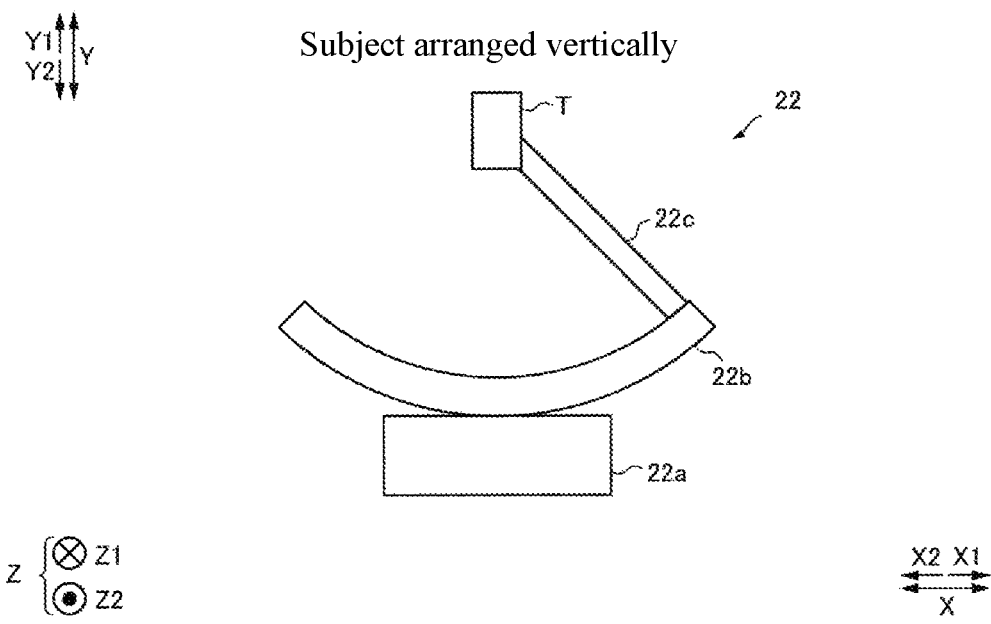
FIG. 11B is a schematic diagram in the case where the subject is arranged vertically by the direction conversion mechanism according to the second embodiment.
Figure 12:
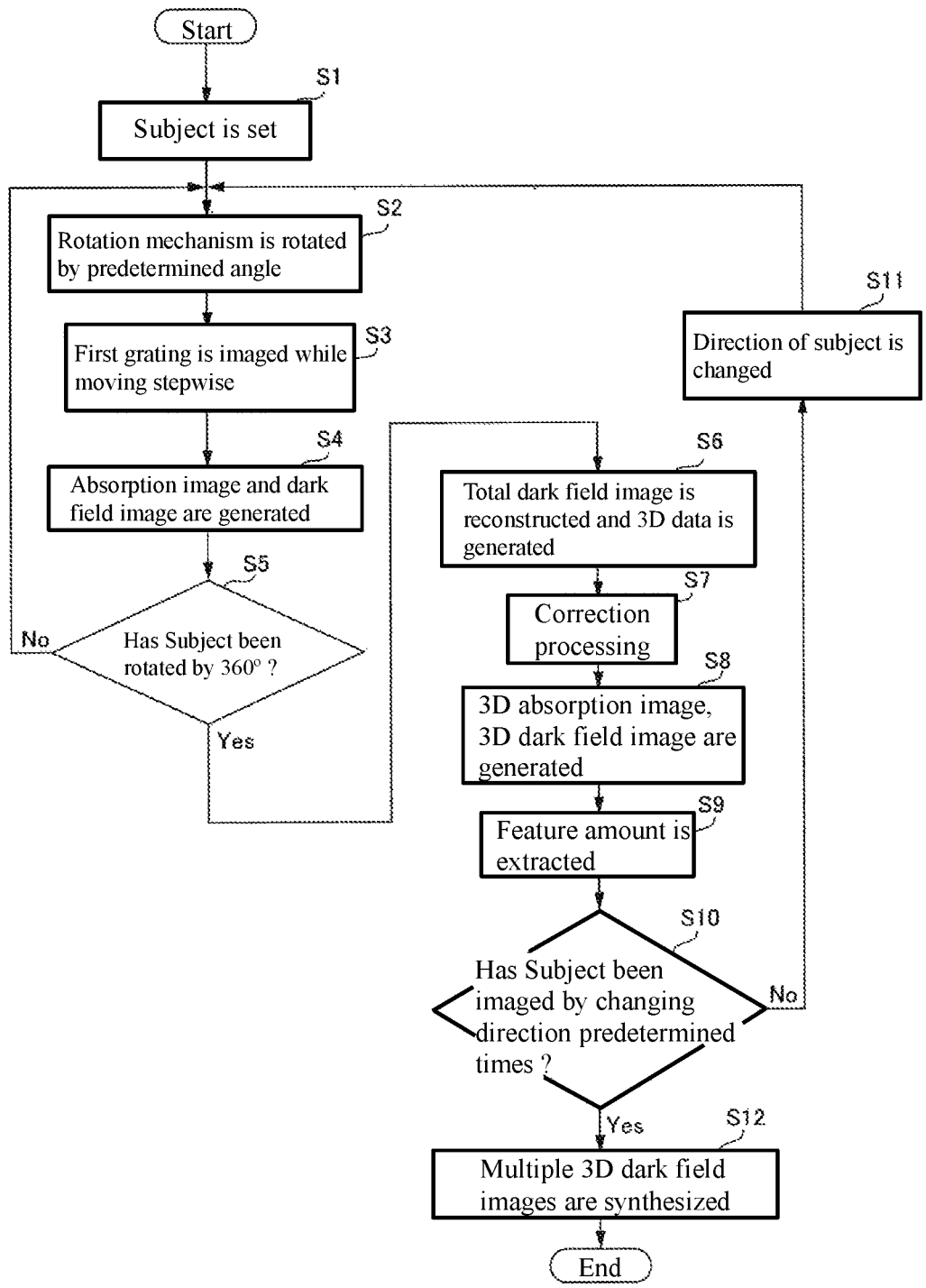
FIG. 12 is a flowchart of an imaging method by the X-ray imaging apparatus according to the second embodiment.
Figure 13:
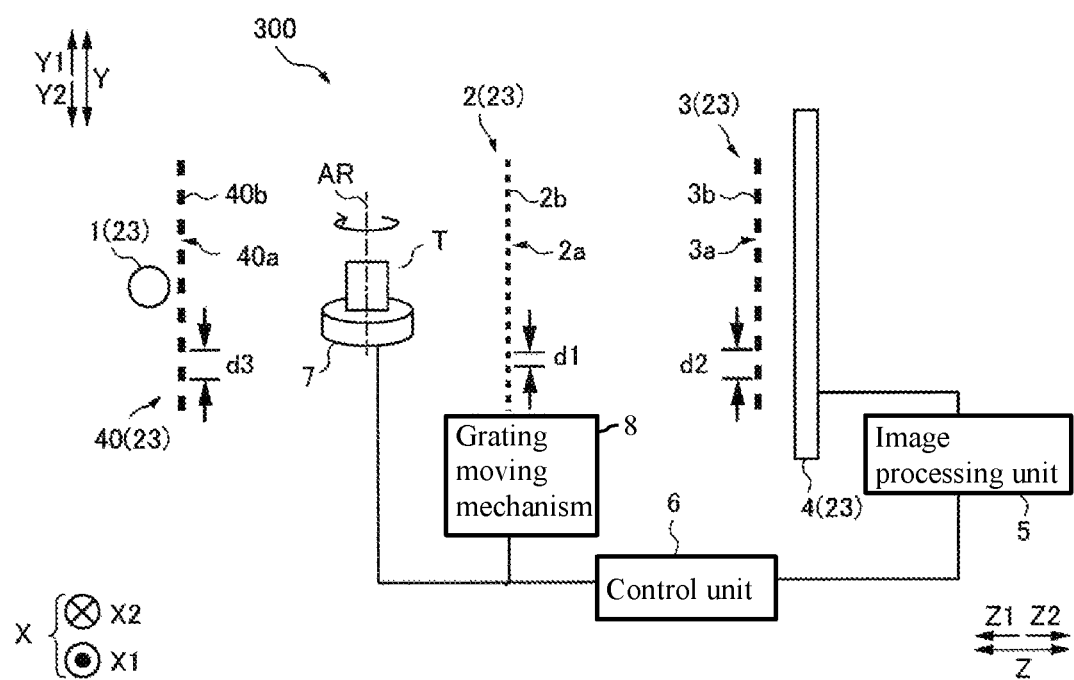
FIG. 13 is a schematic diagram of an X-ray imaging apparatus according to a modification of the first embodiment as viewed from a side.

In the example shown in FIG. 11A and FIG. 11B, the direction changing mechanism 22 rotates the subject holder 22c by 90 degrees in the XY-plane via the drive unit 22a based on the signal from the control unit 60 to thereby change the orientation of the subject T from the state of holding the subject T horizontally to the state of holding the subject T vertically.

(Imaging Method of Subject)

Next, with reference to FIG. 12, the flow of the method of imaging the subject T by the X-ray imaging apparatus 200 according to the second embodiment will be described. The description of Steps similar to those of the first embodiment will be omitted.

In the subject T, a plurality of fiber bundles 10 extending in different directions are included. Under the circumstances, in the second embodiment, the image processing unit 5 is configured to separately extract the three-dimensional data of the fiber bundle 10 extending in different directions from the three-dimensional data of the dark field image 13 captured plural times by changing the direction of the subject T so that different directions of the subject T are along the grating directions of the plurality of gratings. In the second example, the orientation of the subject T is changed by the direction changing mechanism 22.

Specifically, in Steps S1 to S9, the subject T is imaged while rotating 360 degrees to generate a three-dimensional dark field image 21. Thereafter, the process proceeds to Step S10.

In Step S10, the control unit 60 determines whether or not imaging has been performed a predetermined number of times by changing the grating direction of the plurality of gratings and the orientation of the subject T. When imaging has not been performed a predetermined number of times by changing the grating direction of the plurality of gratings and the orientation of the subject T, the process proceeds to Step S11. When imaging has been performed a predetermined number of times by changing the grating direction of the plurality of gratings and the orientation of the subject T, the process proceeds to Step S12.

In Step S11, the control unit 6 changes the grating direction of the plurality of gratings and the orientation of the subject T via the direction changing mechanism 22. In the second embodiment, for example, as shown in FIG. 11, by changing the subject T from a horizontal state to a vertical state, the grating direction of the plurality of gratings and the orientation of the subject T are changed. Thereafter, the process returns to Step S2.

In Step S12, the image processing unit 5 changes the grating direction of the plurality of gratings and the orientation of the subject T and synthesize a plurality of three-dimensional dark field images 21 generated by changing the grating direction of the plurality of gratings and the orientation of the subject T.

Further, in the second embodiment, the image processing unit 5 is configured to separately extract the three-dimensional data of the plurality of fiber bundles 10 extending in different directions from the three-dimensional data of the dark field image 13 captured plural times while relatively changing the grating directions of the plurality of gratings and the orientation of the subject T by the direction changing mechanism 22 and separately generate the three-dimensional dark field image 21 based on the extracted three-dimensional data.

Further, in the second embodiment, the image processing unit 5 is configured to synthesize the plurality of three-dimensional dark field images 21 generated from the plurality of the three-dimensional data based on the fiber bundle 10 extending in mutually different directions. Specifically, the image processing unit 5 separately extracts the fiber bundles 10 extending in mutually different directions. The image processing unit 5 displays the fiber bundles 10 extracted separately from each other. The image processing unit 5 synthesizes the fiber bundles 10 that are distinguishably displayed and extend in mutually different directions as shown in FIG. 2A.

The other configurations of the second embodiment are the same as those of the first embodiment.

Effects of Second Embodiment

In the second embodiment, the following effects can be obtained.

In the second embodiment, as described above, the fiber bundles 10 include fiber bundles 10 extending in a plurality of different directions in the subject, and the image processing unit 5 is configured to extract the three-dimensional data of the fiber bundle 10 extending in different directions from the three-dimensional data of the dark field image 13 captured by changing the orientation of the subject T so that different directions of the subject T are along the grating direction of the plurality of gratings. With this, any one of the plurality of fiber bundles 10 in the subject T can be made to extend along the grating direction of the grating. As a result, in the acquired dark field image 13, the fiber bundles 10 different in direction can be separately visualized.

Further, in the second embodiment, as described above, the X-ray imaging apparatus 200 is further provided with the direction changing mechanism 22 for relatively changing the grating direction of the plurality of gratings and the orientation of the subject T. With this, by using the direction changing mechanism 22, for example, the orientation of the subject T and the grating direction of the plurality of gratings can be easily changed without changing the orientation of the subject T by an operator. As a result, in the dark field image 13, it is possible to visualize the plurality of fiber bundles 10 extending in different directions included in the subject T.

Further, in the second embodiment, as described above, the image processing unit 5 is configured to separately extract the three-dimensional data of the plurality of fiber bundles 10 extending in different directions from the three-dimensional data of the dark field image 13 captured plural times while relatively changing the grating directions of the plurality of gratings and the orientation of the subject T by the direction changing mechanism 22 and separately generate the three-dimensional dark field image 21 based on the extracted three-dimensional data. With this configuration, the dark field image 13 visualizing the plurality of fiber bundles in the subject T can be easily generated.

Further, in the second embodiment, as described above, the image processing unit 5 is configured to synthesize the plurality of three-dimensional dark field images 21 generated from the plurality of the three-dimensional data based on the fiber bundle 10 extending in mutually different directions. With this configuration, it is possible to confirm the plurality of three-dimensional dark field images 21 based on fiber bundles 10 extending in different directions with one three-dimensional image 21, so that it is possible to grasp the plurality of fiber bundles 10 in the subject T in detail.

The other effects of the second embodiment are the same as those of the first embodiment.

(Modifications)

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the first and second embodiments, although an example is shown in which the first grating 2 and the second grating 3 are provided as a plurality of gratings, the present invention is not limited to this. For example, like the X-ray imaging apparatus 300 shown in FIG. 12, a third grating 40 may be provided between the X-ray source 1 and the first grating 2. The third grating 40 has a plurality of slits 40a and X-ray absorption portions 40b arranged at a predetermined period (pitch) d3 in the Y-direction. The slits 40a and the X-ray absorption portions 40b are each formed so as to extend linearly. The slits 40a and the X-ray absorption portions 40b are each formed so as to extend in parallel. Further, the third grating 40 is arranged between the X-ray source 1 and the first grating 2 and is irradiated by the X-rays from the X-ray source 1. The third grating 40 is configured to use the X-rays that have passed through the respective slits 40a as line light sources corresponding to the positions of the respective slits 40a. With this, the third grating 40 can enhance the coherence of the X-rays emitted from the X-ray source 1. With this, the third grating 40 can enhance the coherence of the X-rays emitted from the X-ray source 1. As a result, it is possible to form the self-image of the first grating 2 without depending on the focal length of the X-ray source 1, so that the freedom of selection of the X-ray source 1 can be improved.

Further, in the first and second embodiments, an example is shown in which the rotation mechanism 7 rotates the subject T with respect to the imaging system 23 by rotating the subject T, but the present invention is not limited thereto. For example, it may be configured to rotate the subject T relative to the imaging system 23 by rotating the imaging system 23.

Further, in the second embodiment, an example is shown in which the direction changing mechanism 22 relatively changes the grating direction of the plurality of gratings and the orientation of the subject T by rotating the subject T, but the present invention is not limited thereto. For example, it may be configured to relatively change the grating direction of the plurality of gratings and the orientation of the subject T by holding each grating by the plurality of direction changing mechanisms 22 and rotating each grating. However, when moving gratings, the relative position of each grating may sometimes is displaced. In such a case, it is necessary to finely adjust the grating position. Therefore, it is preferably configured to change the grating direction of the plurality of gratings and the orientation of subject T by changing the orientation of the subject T.

Further, in the second embodiment, an example is shown in which the direction changing mechanism 22 changes the orientation of the subject T from the horizontal state to the vertical state, but the present invention is not limited thereto. The orientation of the subject T may be set to an arbitrary orientation.

Further, in the second embodiment, an example is shown in which the image processing unit 5 separately generates a three-dimensional dark field image 21 when the subject T is arranged horizontally and a three-dimensional dark field image 21 when the subject T is arranged vertically, and the plurality of generated three-dimensional dark field images 21 is synthesized, but the present invention is not limited thereto. A plurality of three-dimensional dark field images 21 may be generated by arranging the subject T at an arbitrary angle other than the horizontal direction and the vertical direction and the generated three-dimensional dark field images 21 are synthesized.

For example, in the first and second embodiments, an example is shown in which the first grating 2 is moved stepwise in a direction orthogonal to the grating direction in the grating plane, but the present invention is not limited to this. Any grating among the plurality of gratings may be moved stepwise.

For example, in the first and second embodiments, an example is shown in which the dark field image 13 is generated by moving the first grating 2 stepwise in a direction orthogonal to the grating direction in the grating plane, but the present invention is not limited to this. For example, it may be configured to generate the dark field image 13 by a moire single shooting technique of capturing images by rotating any one of a plurality of gratings in an XY-plane to form a moire fringe.

For example, in the first and second embodiments, an example is shown in which a phase grating is used as the first grating 2, but the present invention is not limited to this. For example, an absorption grating may be used as the first grating 2.

Further, in the aforementioned first and second embodiments, an example is shown in which a carbon fiber reinforced plastic (CFRP) is imaged as the subject T, but the present invention is not limited to this example. For example, a glass fiber reinforced plastic (GFRP) or the like may be used as the subject. Any subject may be used as long as a fiber bundle is included in the subject to be imaged.

Further, in the first and second embodiments, an example is shown in which the feature amount related to the fiber bundle 10 includes at least one or more of the knitting height H of the fiber bundle 10, the size S of the gap between adjacent fiber bundles 10, the width W of the fiber bundle 10, the length L of the fiber bundle 10, the curvature C of the fiber bundle 10, and the thickness P of the fiber bundle, but the present invention is not limited thereto. For example, the knitting regularity of the fiber bundles 10 may be extracted as the feature amount.

Further, in the second embodiment, an example is shown in which the direction changing mechanism 22 is arranged above the rotation mechanism 7, and the rotation mechanism 7 relatively rotates the subject T together with the direction changing mechanism 22, but the present invention is not limited thereto. For example, it may be configured such that the rotation mechanism 7 is arranged in the subject holder 22c of the direction changing mechanism 22 and the subject T is arranged on the rotation mechanism 7.

In the second embodiment, an example is shown in which the grating direction of the grating is arranged in the horizontal direction (X-direction) and the direction of the axis AR when the subject T is rotated is arranged in the direction orthogonal to the grating direction of the grating (Y-direction), but the present invention is not limited to this. For example, it may be configured such that the grating direction of the grating is arranged in the vertical direction (Y-direction) and the direction of the axis AR when rotating the subject T is arranged in a direction along the grating direction of the grating (Y-direction).

The invention claimed is:
1. An X-ray imaging apparatus comprising:
an X-ray source;
a plurality of gratings including a first grating for forming a self-image by X-rays irradiated from the X-ray source and a second grating for interfering with the self-image of the first grating;
a detector configured to detect the X-rays irradiated from the X-ray source;
a rotation mechanism configured to relatively rotate a subject including a fiber bundle and an imaging system constituted by the X-ray source, the detector, and the plurality of gratings; and
an image processor configured to generate at least a dark field image from an intensity distribution of the X-rays detected by the detector,
wherein the image processor is configured to generate three-dimensional data from a plurality of the dark field images captured at a plurality of rotation angles while relatively rotating the subject and the imaging system by the rotation mechanism and acquire at least three-dimensional dark field image of the subject including the fiber bundle by analyzing X-ray intensity in the generated three-dimensional data, and wherein the image processor is configured to analyze the three-dimensional data to determine a boundary between the subject and a background and extract the three-dimensional data of the fiber bundle in a direction along the grating direction of the plurality of gratings.

2. The X-ray imaging apparatus as recited in claim 1, wherein
the image processor is configured to analyze the X-ray intensity in the generated three-dimensional data to extract the three-dimensional data of the fiber bundle extending in a direction along a grating direction of the plurality of gratings and acquire the three-dimensional dark field image of the subject including the fiber bundle based on the extracted three-dimensional data.

3. The X-ray imaging apparatus as recited in claim 2, wherein
the image processor is configured to extract at least the three-dimensional data of the fiber bundle from the three-dimensional data generated from the dark field image captured by relatively rotating the subject with respect to the imaging system about an axis of a vertical direction orthogonal to a grating direction of the plurality of gratings.

4. The X-ray imaging apparatus as recited in claim 1, wherein
the subject includes fiber bundles extending in a plurality of different directions in the subject, and
the image processor is configured to extract the three-dimensional data of the fiber bundles extending in different directions from the three-dimensional data of the dark field image captured by relatively rotating the subject and the grating direction about the optical axis of the X-rays to change the relative orientation of the subject with respect to the grating direction of the plurality of gratings about the optical axis of X-rays.

5. The X-ray imaging apparatus as recited in claim 1, further comprising a direction changing mechanism configured to change the orientation of the subject with respect to the grating direction of the plurality of gratings by changing at least one of the grating direction of the plurality of gratings and the orientation of the subject with respect to the optical axis of the X-rays,
wherein the rotation mechanism is configured to relatively rotate, about the first axis, the subject and the imaging system with the changed orientation of the subject with respect to the grating direction of the plurality of gratings.

6. The X-ray imaging apparatus as recited in claim 5, wherein
the subject includes a first group of fiber bundles extending in a first extending direction a second group of fiber bundles extending in a second extending direction different than the first extending direction, and
the image processor is configured to, for one of the first group of fiber bundles and second group of fiber bundles, separately extract the three-dimensional data and separately generate the three-dimensional dark field image in dependence on the first and second extending directions.

7. The X-ray imaging apparatus as recited in claim 6, wherein
the image processor is configured to separately synthesize a plurality of three-dimensional dark field images for the one of the first group of fiber bundles and the second group of fiber bundles based on the first group of fiber bundles and second group of fiber bundles extending in mutually different directions.

8. The X-ray imaging apparatus as recited in claim 1, wherein
the image processor is configured to obtain a feature amount related to the fiber bundle in the subject, and
the feature amount related to the fiber bundle includes at least one or more of a knitting height of the fiber bundle, a size of a gap between adjacent fiber bundles, a width of the fiber bundle, a length of the fiber bundle, a curvature of the fiber bundle, and a thickness of the fiber bundle.

9. The X-ray imaging apparatus as recited in claim 8, wherein
the image processor is configured to perform correction processing including at least smoothing processing on the generated three-dimensional data before acquiring the feature amount.

10. The X-ray imaging apparatus as recited in claim 1, wherein
the image processor is configured to highlight boundaries of a plurality of fiber bundles and acquire one or more of the number of the fiber bundles in an area-of-interest of the subject, a distance between boundaries of adjacent fiber bundles, a surface area of the fiber bundles, a density of the fiber bundles based on the boundaries of the fiber bundles.

11. The X-ray imaging apparatus as recited in claim 1, wherein
the plurality of gratings further includes a third grating arranged between the X-ray source and the first grating.

12. The X-ray imaging apparatus as recited in claim 1, further comprising a grating moving mechanism configured to move the grating stepwise,
wherein the grating moving mechanism is configured to move one of the gratings among the plurality of grating stepwise in a direction orthogonal to the grating direction.

13. An X-ray imaging apparatus comprising:
an X-ray source;
a plurality of gratings including a first grating for forming a self-image by X-rays irradiated from the X-ray source and a second grating for interfering with the self-image of the first grating;
a detector configured to detect the X-rays irradiated from the X-ray source;
a rotation mechanism configured to relatively rotate a subject including a fiber bundle and an imaging system constituted by the X-ray source, the detector, and the plurality of gratings; and
an image processor configured to generate at least a dark field image from an intensity distribution of the X-rays detected by the detector, wherein
the image processor is configured to generate three-dimensional data from a plurality of the dark field images captured at a plurality of rotation angles while relatively rotating the subject and the imaging system by the rotation mechanism and acquire at least three-dimensional dark field image of the subject including the fiber bundle by analyzing X-ray intensity in the generated three-dimensional data, and
the image processor is configured to detect a boundary between the fiber bundle and a background, and highlight the detected boundary between the fiber bundle and the background.

* * * * *